United States Patent
Suh et al.

(10) Patent No.: US 9,511,068 B2
(45) Date of Patent: Dec. 6, 2016

(54) COMPOSITION FOR TREATING OR PREVENTING DISEASES CAUSED BY VASCULAR PERMEABILITY, CONTAINING IMATINIB OR PHARMACEUTICALLY ACCEPTABLE SALT THEREOF AS ACTIVE INGREDIENT

(71) Applicant: AJOU UNIVERSITY INDUSTRY - ACADEMIC COOPERATION FOUNDATION, Suwon-si, Gyeonggi-do (KR)

(72) Inventors: Won Hee Suh, Seongnam-si (KR); Ji Yeon Kim, Suwon-si (KR)

(73) Assignees: Ajou University Industry-Academic, Suwon-si, Gyeonggi-do (KR); Cooperation Foundation (KR)

( * ) Notice: Subject to any disclaimer, the term of this patent is extended or adjusted under 35 U.S.C. 154(b) by 0 days.

(21) Appl. No.: 14/409,441

(22) PCT Filed: Jun. 10, 2013

(86) PCT No.: PCT/KR2013/005068
§ 371 (c)(1),
(2) Date: Dec. 18, 2014

(87) PCT Pub. No.: WO2013/191401
PCT Pub. Date: Dec. 27, 2013

(65) Prior Publication Data
US 2015/0320750 A1 Nov. 12, 2015

(30) Foreign Application Priority Data
Jun. 18, 2012 (KR) .................. 10-2012-0065193

(51) Int. Cl.
*A61K 31/506* (2006.01)
*C07D 401/04* (2006.01)

(52) U.S. Cl.
CPC ........... *A61K 31/506* (2013.01); *C07D 401/04* (2013.01)

(58) Field of Classification Search
None
See application file for complete search history.

(56) References Cited

U.S. PATENT DOCUMENTS

| | | | |
|---|---|---|---|
| 5,521,184 A | 5/1996 | Zimmermann | |
| 7,767,688 B2 | 8/2010 | Alland et al. | |
| 8,293,745 B2 | 10/2012 | Riviere et al. | |
| 2005/0203013 A1 | 9/2005 | Soker et al. | |
| 2006/0275260 A1 | 12/2006 | Riviere et al. | |
| 2008/0003219 A1 | 1/2008 | Peyman | |
| 2008/0015205 A1 | 1/2008 | Wedge | |
| 2008/0119479 A1 | 5/2008 | Wedge | |
| 2008/0312252 A1 | 12/2008 | Alland et al. | |
| 2009/0325977 A1 | 12/2009 | Wedge | |
| 2010/0069398 A1 | 3/2010 | Wedge | |
| 2010/0190800 A1 | 7/2010 | Alland et al. | |
| 2012/0295917 A1 | 11/2012 | Kim et al. | |

FOREIGN PATENT DOCUMENTS

| | | |
|---|---|---|
| CN | 101027059 A | 8/2007 |
| CN | 101594851 A | 12/2009 |
| RU | 2009148985 A | 8/2011 |
| WO | 2005020972 A2 | 3/2005 |
| WO | 2006/035204 A2 | 4/2006 |
| WO | 2006035203 A1 | 4/2006 |
| WO | 2006035204 A2 | 4/2006 |
| WO | 2008/055965 A1 | 5/2008 |
| WO | 2008/055966 A1 | 5/2008 |
| WO | 2008/154262 A1 | 12/2008 |
| WO | 2010139678 A1 | 12/2010 |

OTHER PUBLICATIONS

Grunwald et al., "Chronic Myelogenous Leukemia and Retinopathy Treated with Imatinib", Retinal Cases & Brief Reports, 5:366-368 (2011).
Deininger et al., "Specific Targeted Therapy of Chronic Myelogenous Leukemia with Imatinib", Pharmacological Reviews, 55(3):401-423 (2003).
European Search Report for corresponding European Application No. 13807815.9, dated Jan. 5, 2016.
Dafni et al., "Macromolecular Dynamic Contrast-Enhanced (DCE)-MRI Detects Reduced Vascular Permeability in a Prostate Cancer Bone Metastasis Model Following Anti-Platelet-Derived Growth Factor Receptor (PDGRF) Therapy, Indicating a Drop in Vascular Endothelial Growth Factor Receptor (VEGFR) Activation", Magnetic Resonance in Medicine, 60:822-833 (2008).
Aman et al., "The Anticancer Drug Imatinib Protects Against Endothelial Barrier Dysfunction", Regulators of the Lung Endothelial Barrier, American J. Resp. Crit. Care Med., 183(1) Supp. (2011).
Japanese Office Action for Japanese application counterpart No. 2015112601248000, dated Dec. 1, 2015.
Russian Office Action for Russian application counterpart No. 201415382/15 (082265), dated Mar. 1, 2016.

*Primary Examiner* — Michael Barker
(74) *Attorney, Agent, or Firm* — McDonnell Boehnen Hulbert & Berghoff LLP

(57) ABSTRACT

The present invention relates to a pharmaceutical composition for treating or preventing diseases caused by vascular permeability, containing imatinib, which has been conventionally used as an agent for treating chronic myeloid leukemia, or a pharmaceutically acceptable salt thereof as an active ingredient, and a method for treating disease caused by vascular permeability using the composition. The pharmaceutical composition for treating or preventing diseases caused by vascular permeability of the present invention contains imatinib, which has been conventionally used as an agent for treating chronic myeloid leukemia, as an active ingredient, so as to provide a novel use of imatinib and to be able to effectively treat or prevent diseases caused by vascular permeability, and thus may be widely applied to develop a novel agent for treating diseases caused by vascular permeability.

4 Claims, 1 Drawing Sheet

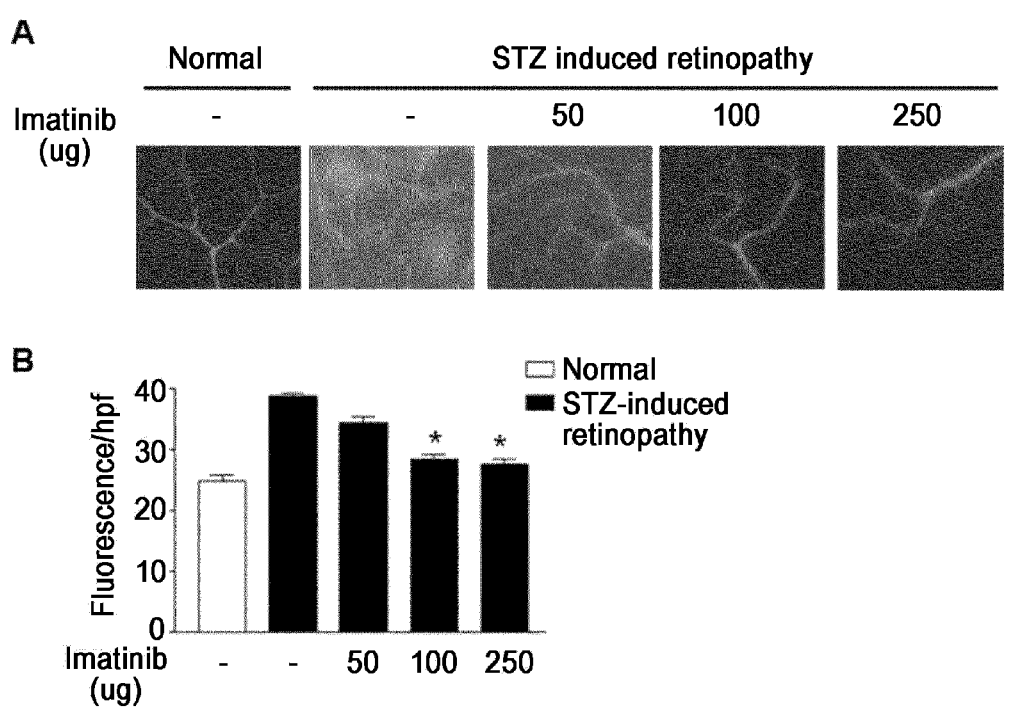

COMPOSITION FOR TREATING OR PREVENTING DISEASES CAUSED BY VASCULAR PERMEABILITY, CONTAINING IMATINIB OR PHARMACEUTICALLY ACCEPTABLE SALT THEREOF AS ACTIVE INGREDIENT

TECHNICAL FIELD

The present invention relates to a pharmaceutical composition for treating or preventing a vascular permeability-related disease, which contains imatinib or a pharmaceutically acceptable salt thereof as an active ingredient, and more particularly, to a pharmaceutical composition for treating or preventing a vascular permeability-related disease, which contains, as an active ingredient, imatinib or a pharmaceutically acceptable salt thereof, which has been used as a therapeutic agent for chronic myelogenous leukemia in the prior art, and to a method of treating a vascular permeability-related disease using the composition.

BACKGROUND ART

Blood vessels are organs essential for the survival and maintenance of normal functions of all types of cells in the human body. Particularly, vascular endothelial cells that are found in the innermost part of blood vessels are present as a single layer and form a cellular barrier that controls the leakage of blood proteins, fluids and electrolytes into the surrounding tissues. The gaps between vascular endothelial cells are very narrow in normal blood vessels, and thus the permeability of the blood vessels is low. However, when blood vessels are infiltrated by inflammatory cells or damaged to cause hypoxia, the secretion of various cytokines and growth factors such as vascular endothelial growth factor (VEGF) significantly increases. Particularly, VEGF stimulates the proliferation, survival and migration of vascular endothelial cells to promote angiogenesis, and at the same time, significantly increases vascular permeability by increasing the gap between vascular endothelial cells. Thus, blood vessels formed by the over-expression of VEGF are characterized in that the leakage of fluids into the surrounding tissues increases.

An excessive increase in vascular permeability causes various diseases. Particularly, an excessive increase in vascular permeability in retina or choroid stimulates hemorrhage and macular edema, and thus is the most common cause of fatal visual loss. Typical diseases that are caused by this pathogenic mechanism include diabetic retinopathy (DR), diabetic macular edema (DME), age-related macular degeneration (AMD), choroidal neovascularization, retinopathy of prematurity (ROP), and the like. Macular edema occurs in 2-6% of patients with mild diabetic retinopathy, 20-63% of patients with moderate diabetic retinopathy, and 70% or more of patients with severe diabetic retinopathy. Once macular edema occurs, the loss of vision appears in about 50% of the patients. In order to prevent serious visual impairment or loss from being caused by diabetes, methods of treating and inhibiting macular edema by reducing capillary leakage have been attempted, and it was reported that, when the activity of VEGF that increases vascular permeability is inhibited, the effect of inhibiting angioedema appears. Known methods for inhibiting the activity of VEGF include a method of reducing vascular permeability by inhibiting the activity of VEGF receptor using antibodies (Bevacizumab, Ranibizumab, etc.) that bind directly to VEGF, a method of inhibiting macular edema using PKC (protein kinase C) inhibitors (ruboxistaurin, etc.) that induce the endocytosis of vascular endothelial tight junction molecules, and a method of simultaneously inhibiting VEGF receptors and Src (soluble tyrosine kinase) that is involved in the signaling pathways of VEGF and VEGF receptors to increase retinal vascular permeability. However, studies on the regulation of angiogenesis and vascular permeability, conducted to date, have mostly been limited to VEGF or VEGF receptors, and have mostly been focused on the development of inhibitors against the genes. Thus, studies on the regulation of angiogenesis and vascular permeability are still insufficient.

DISCLOSURE

Technical Problem

The present inventors have made extensive efforts to find substances for treating vascular permeability-related diseases among ocular diseases, and as a result, have found that imatinib or a pharmaceutically acceptable salt thereof, which has been used as a therapeutic agent for chronic myelogenous leukemia in the prior art, can reduce vascular permeability, and thus can be used as an agent for treating a vascular permeability-related disease, thereby completing the present invention.

Technical Solution

It is an object of the present invention to provide a pharmaceutical composition for treating or preventing a vascular permeability-related disease, which contains imatinib or a pharmaceutically acceptable salt thereof as an active ingredient.

Another object of the present invention is to provide a method of treating a vascular permeability-related disease using the composition.

Advantageous Effects

A pharmaceutical composition for treating or preventing a vascular permeability-related disease according to the present invention contains, as an active ingredient, imatinib that has been used as a therapeutic agent for chronic myelogenous leukemia in the prior art. Thus, the present invention provides the novel use of imatinib. In addition, the pharmaceutical composition of the present invention can effectively treat or prevent a vascular permeability-related disease, and thus can be widely used for the development of novel agents for treating vascular permeability-related diseases.

DESCRIPTION OF DRAWINGS

FIG. 1 depicts a photograph and graph showing the results of analyzing the therapeutic effect of imatinib mesylate on rat models having diabetic retinopathy that is an increased vascular permeability-related disease. FIG. 1(A) is a photograph showing the effect of imatinib mesylate on a reduction in vascular permeability at varying concentrations of imatinib mesylate, and FIG. 1(B) is a graph showing the effect of imatinib mesylate on a reduction in vascular permeability at varying concentrations of imatinib mesylate.

BEST MODE

To achieve the above objects, in one aspect, the present invention provides a pharmaceutical composition for treating or preventing a vascular permeability-related disease, which contains imatinib or a pharmaceutically acceptable salt thereof as an active ingredient.

The present inventors have conducted various studies to find substances for treating vascular permeability-related diseases among ocular diseases, and have paid attention to the novel use of imatinib that has been used as a therapeutic agent for chronic myelogenous leukemia. Although the therapeutic effects of imatinib against vascular permeability-related diseases have not yet been known, it was reported that imatinib exhibits therapeutic effects against various diseases, such as rheumatoid arthritis and viral hepatitis, in addition to chronic myelogenous leukemia as generally known in the art. Thus, the present inventors expected that imatinib would also exhibit certain therapeutic effects against vascular permeability-related diseases. Accordingly, the present inventors administered imatinib to rat models having diabetic retinopathy (that is an increased vascular permeability-related disease) induced by injecting streptozotocin (STZ), and examined the effects of imatinib. As a result, the present inventors have found that vascular permeability induced by injection of STZ was significantly reduced by administration of imatinib, suggesting that imatinib exhibits the effect of treating or preventing vascular permeability-related diseases such as diabetic retinopathy. Therefore, imatinib or a pharmaceutically acceptable salt thereof according to the present invention may be used as an active ingredient in a composition for preventing or treating vascular permeability-related diseases.

As used herein, the term "imatinib" refers to a compound that is chemically named as 4-(4-methylpiperazin-1-ylmethyl)-N-[4-methyl-3-(4-pyridin-3-yl)pyrimidin-2-ylamino)phenyl]-benzamide. Imatinib is known as a therapeutic agent against chronic myelogenous leukemia, which binds to the ATP binding site of tyrosine kinase, the expression of which is induced by Bcr-Abl gene, to specifically inhibit the activity of tyrosine kinase. Imatinib mesylate that is a pharmaceutically acceptable salt of imatinib is commercially available under the trade name of Gleevec™ (Novartis Pharmaceuticals, U.S.A.). In addition, imatinib is known to exhibit inhibitory effects against other tyrosine kinases such as platelet-derived growth factor receptor beta (PDGF-beta), Akt (protein kinase B), extracellular signal-regulated kinase 1 and 2 (ERK 1 and ERK2), c-kit and the like. Imatinib is known to have effects on the prevention or treatment of diseases such as rheumatoid arthritis (WO 03/063844) and viral hepatitis (WO 2005/117885), in addition to chronic myelogenous leukemia, but the effects of imatinib against vascular permeability-related diseases have not yet been known. The present inventors have first found that imatinib known as a therapeutic agent against chronic myelogenous leukemia can significantly reduce vascular permeability that increased by vascular permeability-related diseases.

As used herein, the term "pharmaceutically acceptable salt" means a pharmaceutically usable salt among salts composed of cations and anions bound together by electrostatic attraction. For the purpose of the present invention, the term "pharmaceutically acceptable salt" may be understood to mean an acid addition salt or base addition salt of imatinib, which is suitable for the treatment of patients who are expected to develop vascular permeability-related diseases or have developed the diseases.

In the present invention, the pharmaceutically acceptable salt of imatinib is not specifically limited, as long as it can be suitably used for the treatment of patients who are expected to develop a vascular permeability-related disease or have developed the disease. Preferable examples of the pharmaceutically acceptable salt of imatinib include metal salts of imatinib, salts with organic bases, salts with inorganic acids, salts with organic acids, salt with basic or acidic amino acids, and the like. More preferable examples of the pharmaceutically acceptable salt of imatinib include metal salts such as alkali metal salts (sodium salt, potassium salt, etc.), alkaline earth metal salts (calcium salt, magnesium salt, barium salt, etc.), aluminum salt, etc.; salts with organic salts such as triethylamine, pyridine, picoline, 2,6-lutidine, ethanolamine, diethanolamine, triethanolamine, cyclohexylamine, dicyclohexylamine, N,N'-dibenzylethylenediamine, etc.; salts with inorganic acids such as hydrochloric acid, hydrobromic acid, nitric acid, sulfuric acid, phosphoric acid, etc.; salts with organic acids such as formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, etc.; salts with basic amino acids such as arginine, lysine, ornithine, etc; and salts with acidic amino acids such as aspartic acid, glutamic acid, etc. Most preferably, the pharmaceutically acceptable salt of imatinib may be imatinib mesylate.

As used herein, the term "vascular permeability-related disease" means a disease caused by disruption of the normal regulation of vascular permeability, and generally refers to a disease in which blood vessels are changed to increase vascular permeability to thereby cause hemorrhage. The vascular permeability-related disease is not specifically limited, as long as it can be prevented or treated by the pharmaceutical composition of the present invention. Specific examples of the vascular permeability-related disease include choroidal neovascularization, glaucoma retinitis pigmentosa, retinopathy of prematurity (ROP), proliferative diabetic retinopathy, age-related macular degeneration, glaucoma, corneal dystrophy, retinoschises, Stargardt's disease, autosomal dominant druzen, Best's macular dystrophy, non-proliferative diabetic retinopathy, cystoid macular edema, ischemic retinopathy, inflammation-induced retinal degenerative disease, diabetic macular edema (DME), X-linked juvenile retinoschisis, Malattia Leventinese (ML), Doyne honeycomb retinal dystrophy, endothelial cell-related inflammatory diseases, etc.

As used herein, the term "treatment" or "treating" refers to clinical intervention in an attempt to alter the natural course of the individual or cell being treated, and may be performed either for prophylaxis or during the course of clinical pathology. Desirable effects of the treatment include preventing occurrence or recurrence of disease, alleviation of symptoms, diminishment of any direct or indirect pathological consequences of the disease, preventing metastasis, lowering the rate of disease progression, amelioration or palliation of the disease state, and causing remission or improved prognosis.

In the present invention, "treatment" or "treating" is preferably understood to mean treating a vascular permeability-related disease using imatinib or a pharmaceutically acceptable salt thereof.

As used herein, the term "prevention" or "preventing" means all actions that inhibit or delay the development of vascular permeability-related disease by administering the pharmaceutical composition of the present invention, which contains imatinib or a pharmaceutically acceptable salt thereof as an active ingredient, to a subject expected to develop the disease.

In an example of the present invention, streptozotocin (STZ) was administered to rats to induce diabetic retinopathy that is a vascular permeability-related disease, and imatinib mesylate was administered to the rats. As a result, it was shown that vascular permeability in the rats was significantly reduced (FIG. 1), suggesting that imatinib or a pharmaceutically acceptable salt thereof exhibits therapeutic effects against vascular permeability-related diseases.

Meanwhile, the pharmaceutical composition of the present invention may further contain a suitable carrier, excipient or diluent which is commonly used in the preparation of pharmaceutical compositions. Specifically, the pharmaceutical composition may be formulated in oral dosage forms, including powders, granules, tablets, capsules, suspensions, emulsions, syrup and aerosol, preparations for external application, suppositories, and sterile injectable solutions. Carriers, excipients and diluents that may be contained in the pharmaceutical composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate, and mineral oil. The pharmaceutical composition of the present invention may be formulated with commonly used diluents or excipients, such as fillers, extenders, binders, wetting agents, disintegrants, surfactants, etc. Solid formulations for oral administration include tablets, pills, powders, granules, capsules and the like, and such solid formulations comprise, in addition to imatinib or a pharmaceutically acceptable salt thereof, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like may be used. As the base of the suppositories, witepsol, Macrogol, Tween 61, cacao butter, laurin fat, glycerogelatin and the like may be used.

The content of imatinib or a pharmaceutically acceptable salt thereof in a pharmaceutical composition according to an embodiment of the present invention is not specifically limited, but is preferably 0.0001-50 wt %, and more preferably 0.01-10 wt %, based on the total weight of the composition.

The pharmaceutical composition of the present invention may be administered in a pharmaceutically effective amount. As used herein, the term "pharmaceutically effective amount" refers to an amount sufficient to treat or prevent diseases, at a reasonable benefit/risk ratio applicable to any medical treatment. The effective dosage level of the composition may be determined depending on factors, including the severity of the disease, the activity of the drug, the patient's age, weight, health and sex, the patient's sensitivity to the drug, the time of administration of the composition of the present invention, the route of administration of the composition, excretion rate, the duration of treatment, drugs used in combination with the composition, and other factors known in the medical field. The pharmaceutical composition of the present invention may be administered individually or in combination with other therapeutic agents, and may be administered sequentially or simultaneously with conventional therapeutic agents. The composition may be administered in a single or multiple dosage form. It is important to administer the composition in the minimum amount that can exhibit the maximum effect without causing side effects, in view of all the above-described factors.

The dosage of the pharmaceutical composition of the present invention can be determined by a person skilled in the art in view of the intended use, the severity of the disease, the patient's age, weight, sex and anamnesis, or the kind of substance that is used as an active ingredient. For example, the pharmaceutical composition of the present invention, which contains imatinib or a pharmaceutically acceptable salt thereof, may be administered to mammals, including humans, in a daily dosage of 1-20 mg/kg, and preferably 1-10 mg/kg. The daily dosage of the composition of the present invention is not specifically limited, but may be taken in a single dose or may be divided into several doses.

In another aspect, the present invention provides a method for preventing or treating a vascular permeability-related disease, the method comprising administering a pharmaceutically effective amount of a pharmaceutical composition, which contains imatinib or a pharmaceutically acceptable salt thereof as an active ingredient, to a subject that is at risk of developing or has developed the vascular permeability-related disease.

As described above, imatinib or a pharmaceutically acceptable salt thereof according to the present invention can be used as an active ingredient in a pharmaceutical composition for preventing or treating a vascular permeability-related disease, and thus the composition can be used for the prevention or treatment of a vascular permeability-related disease.

As used herein, the term "subject" means all animals (including humans) that are at risk of developing or have developed the vascular permeability-related disease. The vascular permeability-related disease can be alleviated or treated by administering the composition of the present invention to a subject.

As used herein, the term "alleviating" refers to all actions that ameliorate or beneficially change a vascular permeability-related disease by administering the composition of the present invention.

As used herein, the term "administering" means introducing the pharmaceutical composition of the present invention into a subject by any suitable method. The pharmaceutical composition of the present invention may be administered by various mutes, including oral or parenteral routes, as long as it can reach a target tissue.

In the method for treating a vascular permeability-related disease according to the present invention, the pharmaceutical composition of the present invention may be administered by any general mute, as long as it can reach a target tissue. The pharmaceutical composition of the present invention may be administered intraperitoneally, intravenously, intramuscularly, subcutaneously, intradermally, orally, intranasally, intrapulmonarily or intrarectally depending on the intended use, but is not specifically limited thereto. In addition, the composition may be administered using any system capable of delivering the active ingredient to target cells.

MODE FOR INVENTION

Hereinafter, the present invention will be described in further detail with reference to examples. However, these examples are for illustrative purposes only, and the scope of the present invention is not limited to these examples.

Example 1

Effect of Imatinib Mesylate in Animal Models

Sprague Dawley (SD) rats were administered intraperitoneally with streptozotocin (STZ; Sigma) at a dose of 200 mg/kg (control group), or were injected with STZ while the retina of the animal models were treated with 50, 100 or 250 μg of imatinib mesylate (Novartis, Switzerland) (test groups). After one week, the glucose level of the control group was measured, and as a result, the control group showed a glucose level of 300 mg/dL or higher.

Meanwhile, after the animal models (control and test groups) were housed for 2 weeks, the animal models were anesthetized, and fluorescein isothiocyanate (FITC)-labeled dextran was injected intracardiacally so that the fluorescent substance flowed along the blood vessels. After 30 minutes, the retinas of the animal models were extirpated, separated and mounted flat, and the degree of the distribution of the fluorescent substance in the retinas was observed with a fluorescence microscope (FIG. 1). FIG. 1 depicts a photograph and graph showing the results of analyzing the preventive effect of imatinib mesylate on the induction of diabetic retinopathy in the increased vascular permeability-related disease models. Specifically, FIG. 1(A) is a photograph showing the improving effect of vascular permeability depending on treatment concentrations of imatinib mesylate, and FIG. 1(B) is a graph showing the effect on the prevention of the vascular permeability-related disease depending on treatment concentrations of imatinib mesylate. As can be seen in FIG. 1, it was confirmed that in the retina of the STZ-injected animal models (control group, the retinal vascular permeability increased so that the fluorescent substance did leak into the perivascular tissue to induce the diabetic retinopathy. However, in the case of treating with imatinib mesylate at the same time as injection of STZ, it was confirmed that leak degree of the fluorescent substance was significantly reduced to alleviate or prevent the induction of diabetic retinopathy.

From the above results, it could be seen that imatinib mesylate can be used to treat or prevent diabetic retinopathy in which vascular permeability increases.

We claim:

1. A method for treating or preventing a vascular permeability-related disease of retina in a subject that is at risk of developing or has developed the vascular permeability-related disease of the retina-comprising administering a pharmaceutically effective amount of a pharmaceutical composition, which consists of imatinib (4-(4-methylpiperazin-1-ylmethyl)-N-[4-methyl-3-((4-pyridin-3-yl)pyrimidin-2-yl-amino)phenyl]-benzamide) or a pharmaceutically acceptable salt thereof as an active ingredient, wherein the composition optionally further comprises a pharmaceutically acceptable carrier, excipient or diluent.

2. The method of claim 1, wherein the pharmaceutically acceptable salt of imatinib is imatinib mesylate.

3. The method of claim 1, wherein the vascular permeability-related disease is choroidal neovascularization, glaucoma retinitis pigmentosa, retinopathy of prematurity (ROP), diabetic macular edema (DME), age-related macular degeneration, glaucoma, corneal dystrophy, retinoschises, Stargardt's disease, autosomal dominant druzen, diabetic retinopathy, Best's macular dystrophy, cystoid macular edema, ischemic retinopathy, inflammation-induced retinal degenerative disease, X-linked juvenile retinoschisis, Malattia Leventinese (ML), Doyne honeycomb retinal dystrophy, or vascular endothelial cell-related inflammatory diseases.

4. The method of claim 1, wherein the content of imatinib or the pharmaceutically acceptable salt thereof is 0.0001-50 wt % based on the total weight of the composition.

* * * * *